United States Patent
Djennati et al.

(10) Patent No.: US 10,088,357 B2
(45) Date of Patent: Oct. 2, 2018

(54) PHOTOVOLTAIC SENSOR ARRAYS

(71) Applicant: BIO AMD HOLDINGS LIMITED, Cheshire (GB)

(72) Inventors: Nassr-Eddine Djennati, Cheshire (GB); Andrew Mitchell, Lancashire (GB)

(73) Assignee: BIO AMD HOLDINGS LIMITED, Daresbury, Cheshire (GB)

( * ) Notice: Subject to any disclaimer, the term of this patent is extended or adjusted under 35 U.S.C. 154(b) by 712 days.

(21) Appl. No.: 14/390,848

(22) PCT Filed: Apr. 4, 2013

(86) PCT No.: PCT/GB2013/050882
§ 371 (c)(1),
(2) Date: Oct. 6, 2014

(87) PCT Pub. No.: WO2013/150306
PCT Pub. Date: Oct. 10, 2013

(65) Prior Publication Data
US 2015/0060642 A1 Mar. 5, 2015

(30) Foreign Application Priority Data

Apr. 4, 2012 (GB) .................................. 1206063.8

(51) Int. Cl.
*G01J 1/42* (2006.01)
*G01N 21/84* (2006.01)
(Continued)

(52) U.S. Cl.
CPC ............ *G01J 1/42* (2013.01); *G01N 21/8483* (2013.01); *G01R 31/26* (2013.01); *G01R 31/40* (2013.01);
(Continued)

(58) Field of Classification Search
CPC ..... H01L 31/046; H01L 31/042; H01L 31/10; G01N 21/8483; G01R 31/26; G01R 31/40; Y02E 10/50; G01J 1/42
(Continued)

(56) References Cited

U.S. PATENT DOCUMENTS 4,191,794 A * 3/1980 Shirland ........... H01L 31/03365
136/249
7,098,395 B2 * 8/2006 Hiraishi ................ H01L 31/048
136/244
(Continued)

FOREIGN PATENT DOCUMENTS

EP 1484601 A2 8/2004
JP 2002299666 A 10/2002
(Continued)

Primary Examiner — Seung C Sohn
(74) Attorney, Agent, or Firm — Barlow, Josephs & Holmes, Ltd.

(57) ABSTRACT

A photovoltaic sensor array for detecting variations in light intensity is disclosed. The array has a plurality of photo voltaic cells which are electrically independent from one another and formed on a common substrate. Each cell has corresponding positive and negative electrical connections and each cell is arranged to detect light intensity so that variations in light intensity between the cells can be obtained.

14 Claims, 3 Drawing Sheets

(51) Int. Cl.
*H01L 31/046* (2014.01)
*G01R 31/26* (2014.01)
*G01R 31/40* (2014.01)
*H01L 31/042* (2014.01)
*H01L 31/10* (2006.01)

(52) U.S. Cl.
CPC .......... *H01L 31/042* (2013.01); *H01L 31/046* (2014.12); *H01L 31/10* (2013.01); *Y02E 10/50* (2013.01)

(58) Field of Classification Search
USPC ...................................................... 250/203.4
See application file for complete search history.

(56) References Cited

U.S. PATENT DOCUMENTS

| | | | |
|---|---|---|---|
| 7,847,180 B2 * | 12/2010 | Argo | ............... B82Y 10/00 136/243 |
| 2007/0298487 A1 | 12/2007 | Bachur et al. | |
| 2009/0075838 A1 * | 3/2009 | El Gamal | ......... B01L 3/502715 506/12 |

FOREIGN PATENT DOCUMENTS

| | | | | |
|---|---|---|---|---|
| WO | 2008017819 A1 | 2/2008 | | |
| WO | WO 2008017819 A1 * | 2/2008 | ......... | G01N 21/8483 |
| WO | 2011008299 A2 | 1/2011 | | |

* cited by examiner

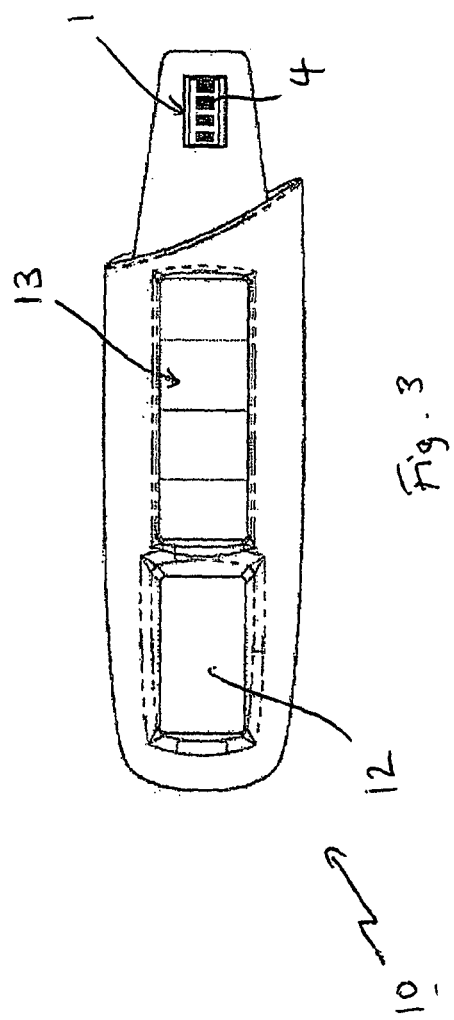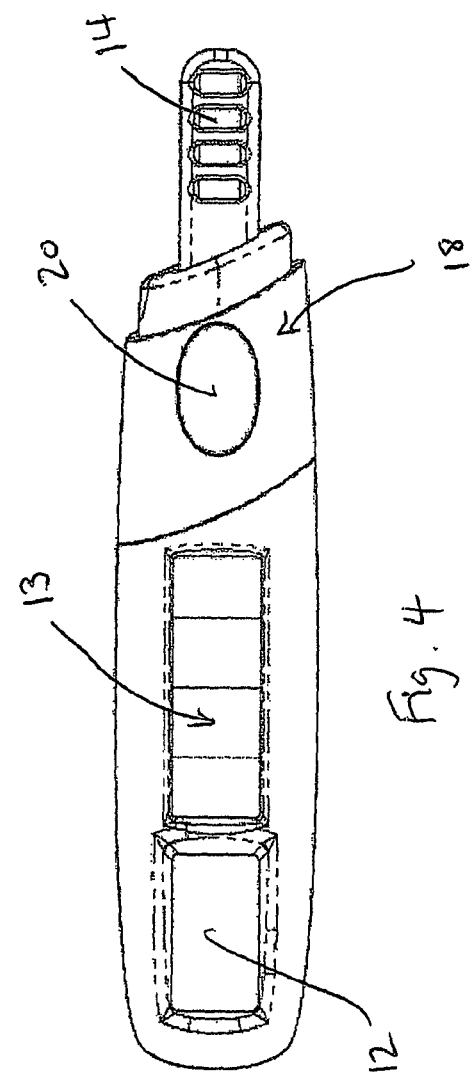

PHOTOVOLTAIC SENSOR ARRAYS

The present invention relates to photovoltaic sensor arrays.

Photovoltaic (PV) cells are commonly used to generate power for a wide range of devices. PV cells typically comprise a semiconductor material such as silicon which has been doped with impurities to create either a p-type material (having a number of "holes" or absence of electrons) or an n-type material (having a net surplus of electrons). These p-type and n-type materials are arranged adjacent one another to form a p-n junction. At the p-n junction interface, in the absence of any external influences, electrons in the n-type material and holes in the p-type material reach equilibrium such that there is no flow of electrons across the junction.

PV cells are arranged to capture electromagnetic radiation from the sun or any other source of light with a particular energy. This absorbed electromagnetic radiation frees electrons in the silicon material so that they can travel across the junction. When electrical conductors are attached to the positive and negative sides of the p-n junction the freed electrons can be captured in the form of an electric current which can be used to power different devices.

Since the amount of light impinging on a PV cell affects the amount of current produced, PV cells can also be used as light sensors to detect changes in light intensity. One useful application of PV cells as light sensors is in assay devices that are used to detect the presence of substances of interest in a sample. WO2008/017819, for example, discloses an assay device having a photovoltaic cell that detects changes in light intensity at a region of the assay device at which substances of interest are arranged to accumulate. As the substances of interest build up at this region, the amount of light transmitted to the photovoltaic cell drops and this, in turn, causes a drop in the amount of voltage generated. This measured drop indicates the presence of the substances of interest. The type of photovoltaic cell typically used is a photodiode which can convert light into either a current or voltage depending upon the mode of operation.

A problem with such photovoltaic cells, however, is that they are relatively complicated and expensive to manufacture and this gives rise to high off the shelf prices with photodiodes typically costing in the region of 25 to 30 cents (USD). Given the quantities of assay devices manufactured, even small savings in individual device manufacture costs can give rise to very large savings overall. A further problem is that, where more than one photodiode is provided to enable comparative measurements to be made, individually packaged photodiodes of the type typically used in assay devices are difficult to align with other photodiodes and can often be manufactured from different silicon wafers. This can give rise to photodiodes having different properties and being subjected to different light conditions which leads to measurement errors.

An object of the present invention is to provide a semiconductor sensor that is cheaper to manufacture and purchase than conventional semiconductor sensors and that can be used in assay devices to accurately detect substances of interest in a sample.

According to a first aspect of the present invention, there is provided a photovoltaic sensor array for detecting variations in light intensity comprising a plurality of photovoltaic cells which are electrically independent from one another and formed on a common substrate, each cell having corresponding positive and negative electrical connections and each cell being arranged to detect light intensity so that variations in light intensity between the cells can be obtained.

Advantageously, forming the cells on a common substrate, such as by depositing the photovoltaic cells using vapour deposition, enables a compact sensor array having a plurality of photovoltaic cells to be manufactured more cheaply than an equivalent number of conventional photodiodes made from a silicon wafer. This is because the manufacturing process involved is simpler and requires less packaging. A sensor array according to the invention can be made for as little as a fifth of the price of an equivalent number of conventional photodiodes used in an immunoassay device. Conventional photodiodes are also too bulky to be arranged in as compact a space as a sensor array according to the invention. Advantageously, having a compact arrangement increases the chances that the photovoltaic cells will experience the same light conditions. This ensures that the comparison between the light intensity detected by the various photovoltaic cells is accurate and minimises interference and abnormality detection. Using vapour deposition also ensures that the properties of the photovoltaic cells are closely similar, in contrast to conventional photodiodes which can comprise photovoltaic cells from different parts of a silicon wafer or even different silicon wafers which can give rise to different properties and therefore inaccurate measurements.

There may be at least three photovoltaic cells. There may be four or more photovoltaic cells. The photovoltaic cells may be arranged in a line. Adjacent photovoltaic cells may be less than 1 mm apart. Adjacent photovoltaic cells may be approximately 0.6 mm apart. Each photovoltaic cell may be formed from amorphous silicon.

At least two photovoltaic cells may be substantially vertically aligned. The upper surfaces of at least two photovoltaic cells may lie along substantially the same plane.

Advantageously, having at least two photovoltaic cells substantially vertically aligned and/or having the upper surfaces of at least two photovoltaic cells lying along substantially the same plane improves the chances of the at least two cells experiencing the same light conditions. This improves the accuracy of any comparison between the amount of light detected by two adjacent cells.

Each photovoltaic cell may be individually connectable to a circuit so that the output of each cell can be independently measured and compared.

The photovoltaic cells may all be substantially the same uniform thickness. The photovoltaic cells may be formed on the common substrate by vapour-deposition.

There may be an immunoassay device comprising a sensor array according to the first aspect of the invention.

In order that the invention may be more clearly understood an embodiment thereof will now be described with reference to the accompanying drawings, of which:

FIG. 3 is a plan view of section of an assay strip reader incorporating a sensor array as shown in FIG. 1;

FIG. 4 is a plan view of the section shown in FIG. 3 with a second section of an assay strip reader connected thereto.

Figure 1:
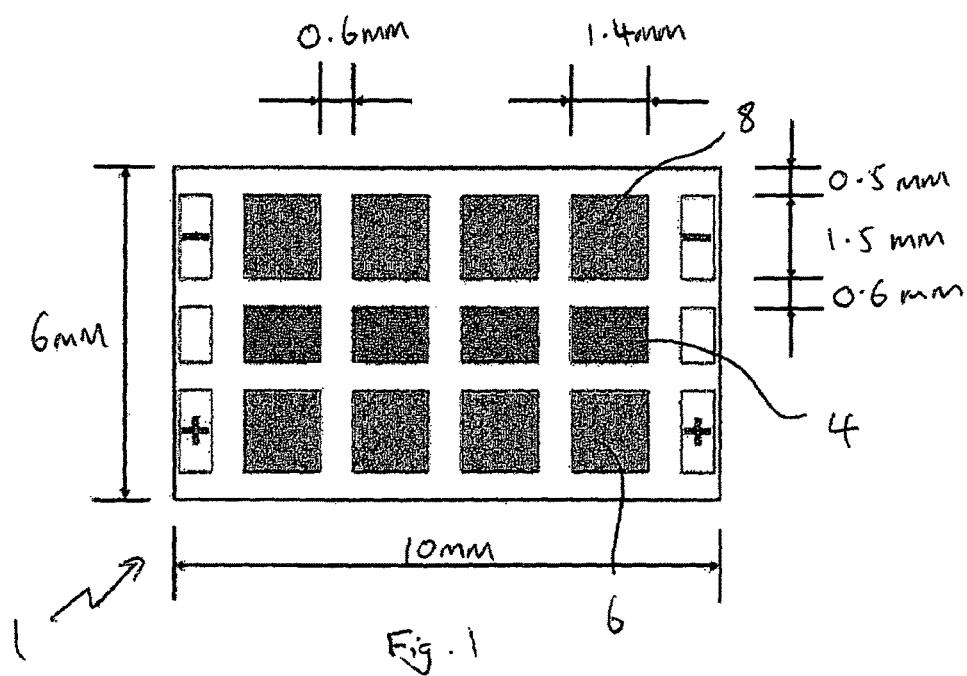
FIG. 1 is a schematic plan view of a sensor array according to the invention.
Figure 2:
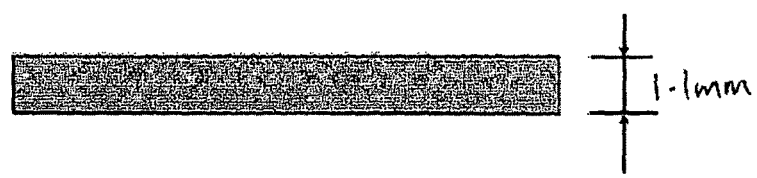
FIG. 2 is a side view of the sensor array shown in FIG. 1.

With reference to the drawings, there is shown a sensor array 1 comprising a substrate 2 made from glass which is approximately 10 mm×6 mm×1.1 mm. Four monolithic amorphous silicon (a-Si) photovoltaic cells 4 are arranged individually in a line along the substrate 2. The cells are spaced apart by around 0.6 mm and are electrically independent from one another. Each cell 4 is vertically aligned so that their top surfaces are substantially parallel and lie along substantially the same plane. This is to ensure they are all exposed to approximately the same light conditions.

Each cell 4 is connected to a positive terminal 6 on one side and a negative terminal 8 on the opposite side respectively of the cell 4. The two terminals are approximately 1.4 m×1.5 mm and are spaced from one edge of the substrate by approximately 0.5 mm. The positive and negative terminals may be spaced from their corresponding cell 4 by approximately 0.6 mm. When the positive 6 and negative 8 terminals are connected to a circuit and the cell 4 is exposed to light having the required energy to knock electrons loose within the semiconductor material, a voltage is generated at the output. The size of voltage generated is dependent upon the amount of light incident on the cell 4. Thus, the amount of light on a particular cell 4 can be detected and compared with the other cells 4 to determine small variations in light intensity across the array.

The array 1 is manufactured by vapour-depositing four thin films of amorphous silicon in a line on the glass substrate 2 to form the four photovoltaic cells 4. The surface of the glass substrate 2 on which the photovoltaic cells 4 are deposited is substantially flat. The silicon deposited on the substrate 2 to form the photovoltaic cells 4 is applied in a thin film of substantially uniform thickness so that the top surface of each photovoltaic cell 4 lies substantially in the same plane. The positive 6 and negative 8 terminals are connected to the p and n sides respectively of the corresponding photovoltaic cell 4 so that the array can be connected to a circuit.

In this embodiment, the photovoltaic cells 4 are manufactured to have an open circuit voltage of 1.5V/cell, a working temperature of approximately −5 to 45° C., a store temperature of approximately −20 to 60° C., store humidity of less than 75% and a scope of intensity of greater than or equal to 200 lux.

Figure 5:
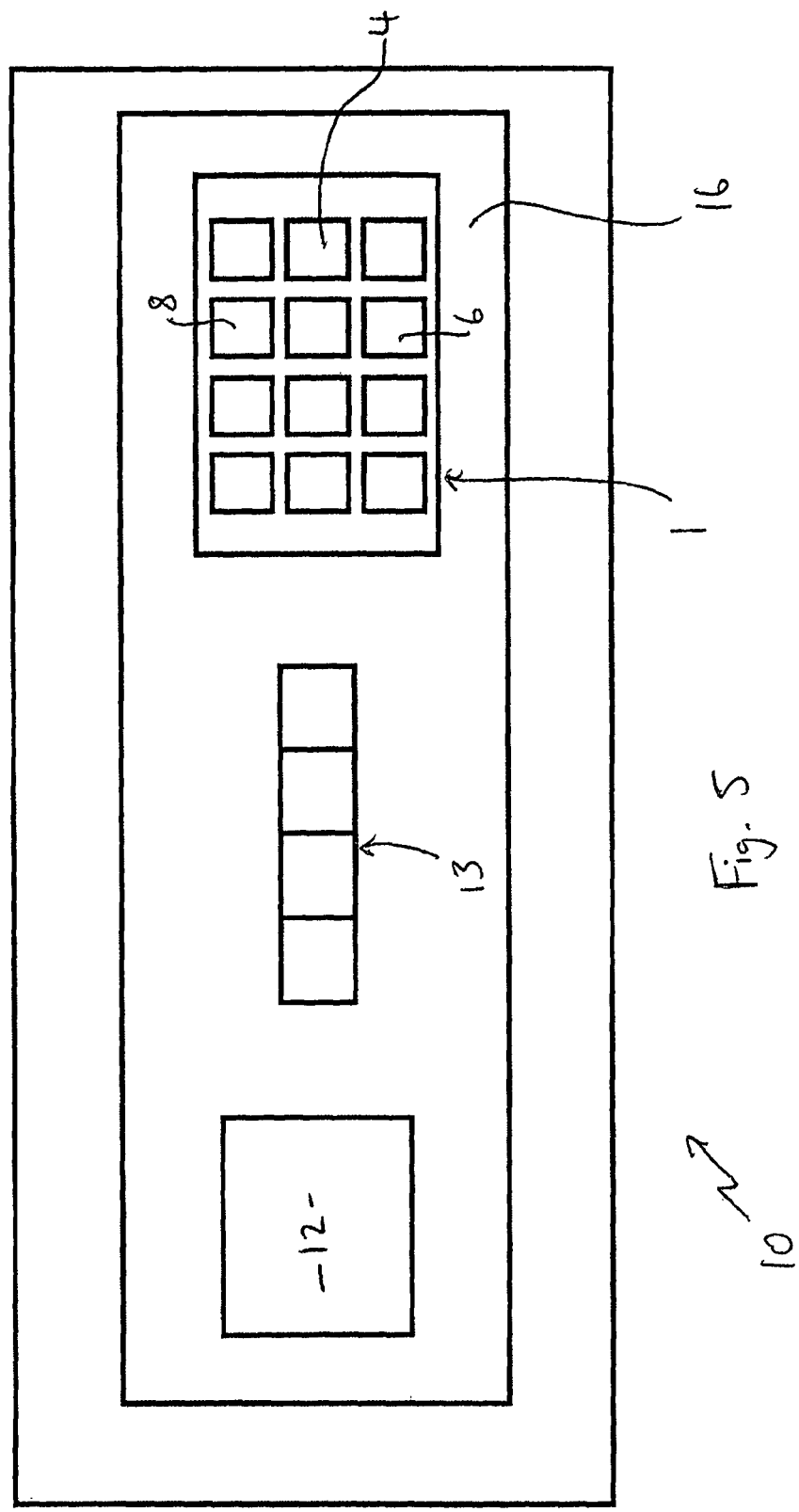
FIG. 5 is a schematic view of the section shown in FIG. 3.

The sensor array 1 is adapted for use with an assay strip reader which can detect the build-up of substances of interest on an assay strip and display the result electronically. A section 10 of a strip reader is shown in FIG. 3 and schematically in FIG. 5. The section 10 comprises a printed circuit board (PCB) 16 which incorporates an LCD display 12 and a photovoltaic module 13 for powering the reader, and which is connectable to the array via the positive 6 and negative 8 terminals. Each cell 4 of the array is independently connected to the PCB 16 so that the voltage output of each cell 4 can be independently measured. The PCB 16 is operative to compare the voltages generated at each cell 4. The array 1 can therefore detect small variations of incident light.

A second section 18 of the reader is connectable to the first section 10 at the region at which the sensor array 1 is exposed. When connected together, the second section 18 is arranged to cover the array 1 but comprises a transparent lens 20 that permits light to strike the solar cells 4 of the array 1. The second section 18 comprises a nitrocellulose strip 14 which is arranged to extend between the lens 20 and the solar array 1 when the two sections 10, 18 are connected together. The strip 14 is exposed at one end of the second section 18 so that a sample can be deposited thereon.

The array 1 is positioned within the first section 10 of the reader so that two of the four cells 4, in this example the first and third, lie beneath regions of the strip 14 at which substances of interest are arranged to deposit and build-up. The first region over the first cell is the control line, indicating whether or not the test has worked successfully, and the second region over the third cell is the test line, indicating whether or not the test produces a positive or negative result. The second and fourth cells are positioned beneath regions of the strip at which no substances are arranged to build-up and serve as reference lines for the first and third cells respectively. Such devices can be used, for example, to determine whether or not a woman is pregnant.

In use, a sample is placed on the exposed strip 14 of the second section 18 when connected to the first section 10 and substances may build up at the first and second regions of the strip 14. The build-up of substances at these regions causes the amount of light incident through the lens 20 on the first and third cells to drop which causes a corresponding drop in voltage across the two cells 4. By comparing the voltage drop across these two cells with the voltage across the second and fourth cells respectively, it is possible to determine variations in light intensity and therefore whether or not a positive result has been achieved. The result can then be displayed on the LCD display 12 of the reader 10.

The array 1 has many different applications. It may be used, for example, as part of lateral flow immunoassay devices and other devices where it is desired to measure the presence of a fluid, or a wave front or meniscus in a fluid. The assay device may be an immunoassay strip.

The array 1 may also be used in conjunction with a micro or nano-fluidic device which comprises single or multiple collection areas or chambers in an assay. In such devices, magnetic particles are attached to, coated on or bonded to a substance of interest and become trapped in the collection chambers where a drop in incident light falling on an array 1 placed under these areas may be detected.

Whilst the array 1 described above may be used to determine whether or not a woman is pregnant, it may also be used to detect substances indicative of, for example, fertility/ovulation, drugs of abuse, cardiac markers and infectious diseases.

It is of course to be understood that the above embodiment has been described by way of example only and that many variations are possible without departing from the scope of the invention as defined by the appended claims.

The invention claimed is:

1. A photovoltaic sensor array for detecting variations in light intensity comprising a plurality of photovoltaic cells which are electrically independent from one another and vapour-deposited onto a common substrate, each cell having corresponding positive and negative electrical connections and each cell being arranged to independently detect light intensity so that variations in light intensity between the cells can be independently obtained.

2. The sensor array as claimed in claim 1, wherein there are at least three photovoltaic cells.

3. The sensor array as claimed in claim 2, wherein there are four photovoltaic cells.

4. The sensor array as claimed in claim 1, wherein the photovoltaic cells are arranged in a line.

5. The sensor array as claimed in claim 1, wherein adjacent photovoltaic cells are less than 1mm apart.

6. The sensor array as claimed in claim 5, wherein adjacent photovoltaic cells are approximately 0.6mm apart.

7. The sensor array as claimed in claim 1, wherein each photovoltaic cell is formed from amorphous silicon.

8. The sensor array as claimed in claim 1, wherein at least two photovoltaic cells are substantially vertically aligned.

9. The sensor array as claimed in claim 1, wherein the upper surfaces of at least two photovoltaic cells lie along substantially the same plane.

10. The sensor array as claimed in claim 1, wherein the respective positive and negative electrical connections of each photovoltaic cell are individually connectable to a circuit so that the output of each cell can be independently measured and compared.

11. The sensor array as claimed in claim 1, wherein the photovoltaic cells are all substantially the same uniform thickness.

12. An immunoassay device comprising a sensor array, the sensor array comprising a plurality of photovoltaic cells which are electrically independent from one another and vapour-deposited onto a common substrate, each cell having corresponding positive and negative electrical connections and each cell being arranged to independently detect light intensity so that variations in light intensity between the cells can be independently obtained.

13. The immunoassay device as claimed in claim 12, wherein the respective positive and negative electrical connections of each photovoltaic cell are individually connectable to a circuit so that the output of each cell can be independently measured and compared.

14. An immunoassay device comprising:
a glass substrate having a flat upper surface;
a photovoltaic sensor array configured and arranged on said upper surface of said glass substrate for detecting variations in light intensity, said array comprising a plurality of photovoltaic cells which are electrically independent from one another and vapour-deposited in a uniform thickness onto said flat upper surface of said glass substrate,
each of said cells having an upper surface lying in a common plane,
each cell having corresponding positive and negative electrical connections respectively connected to a comparator circuit,
each cell being arranged to independently detect light intensity so that variations in light intensity between the cells can be independently measured and compared by said comparator circuit.

\* \* \* \* \*